United States Patent
Tsujii

(10) Patent No.: US 7,023,958 B2
(45) Date of Patent: Apr. 4, 2006

(54) RADIATION IMAGE-ACQUIRING APPARATUS, AND RADIATION IMAGE-ACQUIRING METHOD

(75) Inventor: Osamu Tsujii, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/951,752

(22) Filed: Sep. 27, 2004

(65) Prior Publication Data

US 2005/0074091 A1    Apr. 7, 2005

(30) Foreign Application Priority Data

Oct. 3, 2003    (JP)    ............... 2003-345209

(51) Int. Cl.
*H05G 1/10*    (2006.01)

(52) U.S. Cl. ............... 378/95; 378/8; 378/62

(58) Field of Classification Search .......... 378/4, 378/8, 20, 62, 95, 117
See application file for complete search history.

(56) References Cited

U.S. PATENT DOCUMENTS

2005/0185754 A1*    8/2005    Tsujii ............... 378/8

FOREIGN PATENT DOCUMENTS

JP    2000-51208    2/2000

OTHER PUBLICATIONS

Feldkamp, et al. "Optics and Image Science", Journal of the Optical Society of America A. vol. 1, No. 6. Jun. 1984.

* cited by examiner

*Primary Examiner*—Courtney Thomas
(74) *Attorney, Agent, or Firm*—Morgan & Finnegan, LLP

(57) ABSTRACT

A radiation image-acquiring apparatus or a radiation image-acquiring method capable of reducing artifact due to pulsations of a heart of a subject to be examined is disclosed. X-rays generated by an X-ray generating portion and transmitted through the subject are detected as a two-dimensional distribution by a two-dimensional detector while the subject is rotated by a rotating table in an image-acquiring area formed by the X-ray generating portion and the two-dimensional detector, pulsation variations specific to the subject are detected, and a period p of the variation is calculated. A ratio q of a static time relative to the variation period p is then determined, a rotation time for one rotation is calculated based on the variation period p and the ratio q, and a rotating table is rotated.

8 Claims, 5 Drawing Sheets

C = CONSTRICTION TIME
R = RELAXATION TIME
C = EQUIVALENT RELAXATION TIME

RADIATION IMAGE-ACQUIRING APPARATUS, AND RADIATION IMAGE-ACQUIRING METHOD

BACKGROUND OF THE INVENTION

1. Field of the Invention

The present invention relates to a radiation image-acquiring apparatus or a radiation image-acquiring method capable of removing or reducing influences of motion variations in a subject (a person, for example) to be examined (an examined subject) in, for example, X-ray CT (Computer Tomography) apparatuses for performing image-acquiring by using radiation such as X-rays.

2. Related Background Art

Conventionally, an X-ray CT apparatus is known, in which an examined subject is exposed to X-rays, an X-ray detector detects X-rays transmitted through or scattered by the examined subject, and a transmission image, a tomographic image or a three-dimensional image of the subject is acquired based on this X-ray detection output (the number of photons of the X-rays) from the detector.

In connection with such an X-ray CT apparatus, a cone-beam CT apparatus (CBCT) has been developed. While an X-ray beam is thinly sliced in a Z direction (this sliced beam is called a fan beam) in an ordinary X-ray CT apparatus, an X-ray beam expanding also in the Z direction (referred to as a cone beam) is used in the cone-beam CT.

Further, in addition to a conventional CT with a single row of ROW, a type of the CBCT corresponding to a so-called third-generation type or an R/R type has been studied. In the third-generation CT, scanning and acquisition of projection data are executed while a set of an X-ray generating source and a detector is rotated around an examined subject.

FIG. 6 illustrates an example of the CBCT apparatus that belongs to the third-generation CT apparatus. In this apparatus, an X-ray detector 2 is also rotated around an examined subject P together with an X-ray generating source 1 about a rotational Z-axis, and scanning of a region of interest is completed in a single rotation.

In an ordinary X-ray CT apparatus, elements of a detector are arranged in line along a channel (CH) direction since sampling is performed in the CH direction. Individual elements are distinguished by their channel numbers, respectively. In contrast thereto, in a CBCT apparatus, elements of a detector are also arranged along the Z direction (the ROW direction). In other words, elements of the detector are two-dimensionally arranged in the form of an orthogonal lattice in the X-ray detector 2 of the CBCT apparatus.

In such a CBCT apparatus, the X-ray detector 2 is comprised of detector elements arranged in two directions of the Z direction (the ROW direction) and the CH direction in the form of a lattice, and X-rays are emitted in a conical form with an expansion also in the Z direction, so that projection data in a plurality of rows can be simultaneously obtained collectively.

When a plurality of sliced portions are simultaneously photographed, the cone angle is a problem. In a region wherein the cone angle is large, X-rays transmitted through a section of an examined subject are likely to have artifacts, and accordingly a reconstruction error is likely to occur. To avoid this problem, the following only needs to be carried out. That is, a distance (Focus-Detector-Distance: FDD) between a focal point of X-rays and a flat panel detector (FPD) is enlarged, and the cone angle is decreased.

However, as the distance (FDD) increases, an image-acquiring system increases, and it becomes difficult to speedily rotate an X-ray tube and the FPD. Further, it becomes troublesome to place the apparatus in an examination room. It is therefore considered to slowly rotate an examined subject in place of the rotation of the X-ray tube and the FPD to carry out the image-acquiring.

In the event that a human body is rotated, a period of three (3) to five (5) seconds per rotation is considered appropriate. In the image-acquiring for such a long time, however, motions of internal organs due to pulsations of a heart as well as motions of the human body become problems. Especially, in the image-acquiring of a lung area, motions of blood vessels in lungs are outstanding due to pulsations of the heart. As illustrated in FIG. 7, in a period between an R wave and a T wave of an electrocardiogram, the size of a heart abruptly changes, and a large pressure is applied to an aorta, so that the location of the blood vessel is drastically displaced. Such a drastic displacement of the blood vessel not only lowers the resolution of a reconstructed image, but also brings forth artifact, resulting in troubles to diagnosis of a disease.

Japanese Patent Application Laid-Open No. 2000-51208 (JPLO-2000-51208) discloses an X-ray CT apparatus capable of achieving both reduction of the radiation dose of X-ray exposure and prevention of degradation of an image in an electrocardiogram synchronous scanning. This apparatus includes a high-voltage generator for applying a high voltage to an X-ray tube to emit X-rays from the X-ray tube, an X-ray detector for detecting X-rays coming from the X-ray tube through an examined subject, a tomographic-image reconstructing processor for reconstructing a tomographic image based on projection data detected by the detector, an electrocardiograph for measuring an electrocardiogram of the examined subject, and a system controller for controlling the high-voltage generator based on the electrocardiogram such that generation of X-rays can be stopped in a predetermined time within a pulsation cycle of the examined subject and X-rays can be generated in a time other than the predetermined period.

In the apparatus of the Japanese Patent Application Laid-Open No. 2000-51208, a period of the pulsation is morphologically classified into a constriction time, a relaxation time and an equivalent relaxation time, and data is acquired by exposure of X-rays performed in the equivalent relaxation time in which morphological variation is small. It is here assumed that a scanning rate is 0.75 second per rotation, and acquisition of data is executed in a half scanning. On the assumption that a fan angle is 50 degrees, a relation of 0.75(180+50)/360=0.48 (second) holds. In other words, when the equivalent relaxation time is equal to or less than 0.48 second, the half-scanning acquisition of data in the equivalent relaxation time is completed in one rotation.

The length of the equivalent relaxation time will be examined. In the Japanese Patent Application Laid-Open No. 2000-51208, a pulsation period is assumed to be about 1 (second), and it can be seen from FIG. 7 that the equivalent relaxation time can occupy over about 60 percent of one period of the pulsation. Accordingly the equivalent relaxation time lasts about 0.6 second. In short, an invention of the Japanese Patent Application Laid-Open No. 2000-51208 is accomplished on the above-discussed assumption, and a patient is dosed with a β blocker and requested to keep quiet for about a hour to achieve the number of pulsations of 60 times per second.

As discussed above, however, when a stand-up CBCT using a large-sized FPD is considered, a period of over three to five seconds per rotation is needed to rotate the examined subject. Therefore, the invention disclosed in the Japanese Patent Application Laid-Open No. 2000-51208 cannot be applied to a CBCT of that type.

SUMMARY OF THE INVENTION

It is an object of the present invention to provide a radiation image-acquiring apparatus or a radiation image-acquiring method capable of removing or reducing influences of variations present in a subject to be examined (an examined subject).

In order to achieve the above object, for example, a radiation image-acquiring apparatus of the present invention comprises the following arrangement.

That is, a radiation image-acquiring apparatus comprising: X-ray generating means; two-dimensional detecting means adapted to receive X-rays transmitted through an examined subject and converting them into image data; rotating means adapted to relatively rotate the examined subject in an image-acquiring area formed by the X-ray generating means and the two-dimensional detecting means; variation detecting means adapted to detect a predetermined variation of the examined subject; period calculating means adapted to calculate a period p of the variation detected by the variation detecting means; and static-ratio determining means adapted to determine a ratio q of a static time relative to the period p from the variation detected by the variation detecting means, wherein rotation-time calculating means calculates a rotation time t for one rotation of the rotating means based on the period p and the ratio q.

In order to achieve the above object, for example, a radiation image-acquiring method of the present invention comprises the following arrangement.

That is, a radiation image-acquiring method performed in a radiation image-acquiring apparatus including X-ray generating means, two-dimensional detecting means adapted to receive X-rays transmitted through an examined subject and converting them into image data, and rotating means adapted to relatively rotate the examined subject in an image-acquiring area formed by the X-ray generating means and the two-dimensional detecting means, the method comprising: a step of detecting a predetermined variation of the examined subject; a step of calculating a period p of the variation detected in the variation detecting step; and a step of determining a ratio q of a static time relative to the period p from the variation detected in the variation detecting step, wherein a rotation time t for one rotation of the rotating means is calculated based on the period p and the ratio q in a rotation-time calculating step.

Other features and advantages of the present invention will be apparent from the following descriptions taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the descriptions, serve to explain the principle of the invention.

DETAILED DESCRIPTION OF THE PREFERRED EMBODIMENTS

Preferred embodiments of the present invention will now be described in detail in accordance with the accompanying drawings.

Figure 1:
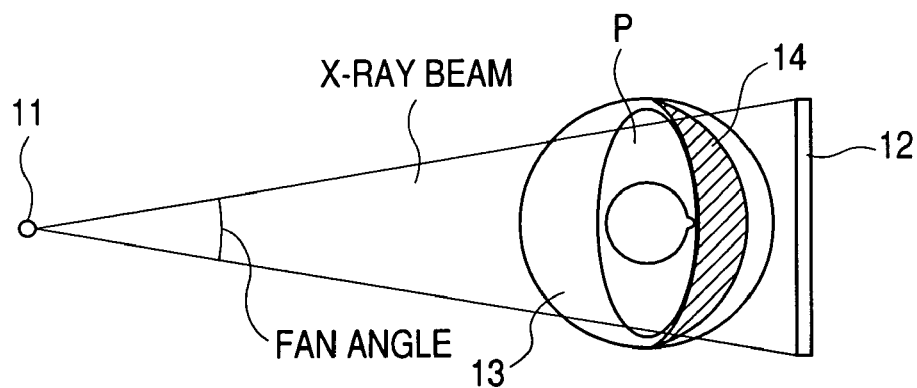
FIG. 1 is a plan view illustrating an embodiment of the present invention.
Figure 2:
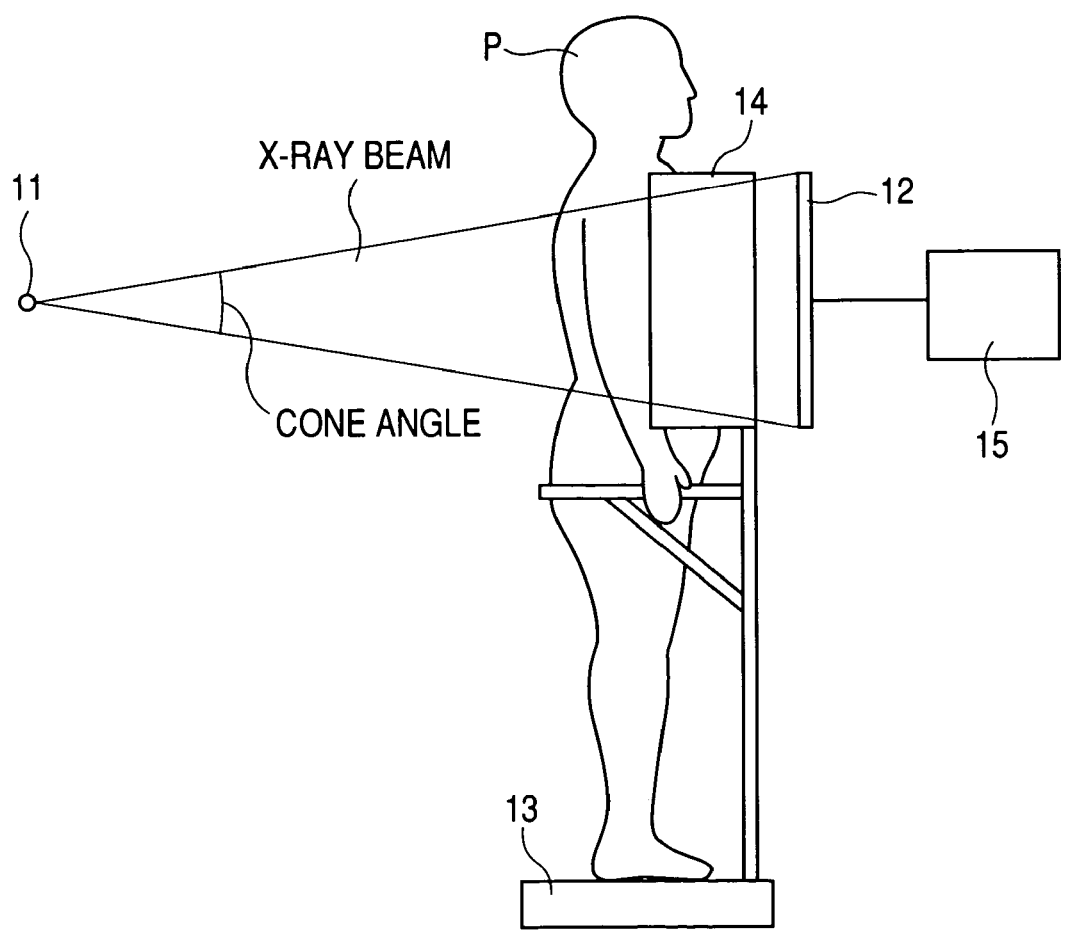
FIG. 2 is a side view illustrating the embodiment of FIG. 1.

FIG. 1 is a plan view illustrating an embodiment of the present invention, and FIG. 2 is a side view thereof. An examined subject or person P takes a position between an X-ray generating portion 11 and a two-dimensional detector 12. The examined person P rides on a-rotating table 13, and a chest portion of the examined person P is brought into contact with a chest plate 14 attached to the rotating table 13. In the two-dimensional detector 12, each pixel has a size of 250 (microns)×250 (microns), and the total number of pixels is 1720×1720 (pixels). The two-dimensional detector 12 is comprised of a semiconductor sensor having a peripheral configuration of 43 (cm)×43 (cm). An output of the two-dimensional detector 12 is connected to a reconstruction portion 15 through a BUS (described later).

X-rays emitted from the X-ray generating portion 11 are transmitted through the examined person P, the chest plate 14 and a scattered-ray removing grid (not shown) in this order, and reach the two-dimensional detector 12. Data acquired by the two-dimensional detector 12 is transferred to the reconstruction portion 15, and a reconstruction process of producing a tomographic image is carried out.

Figure 3:
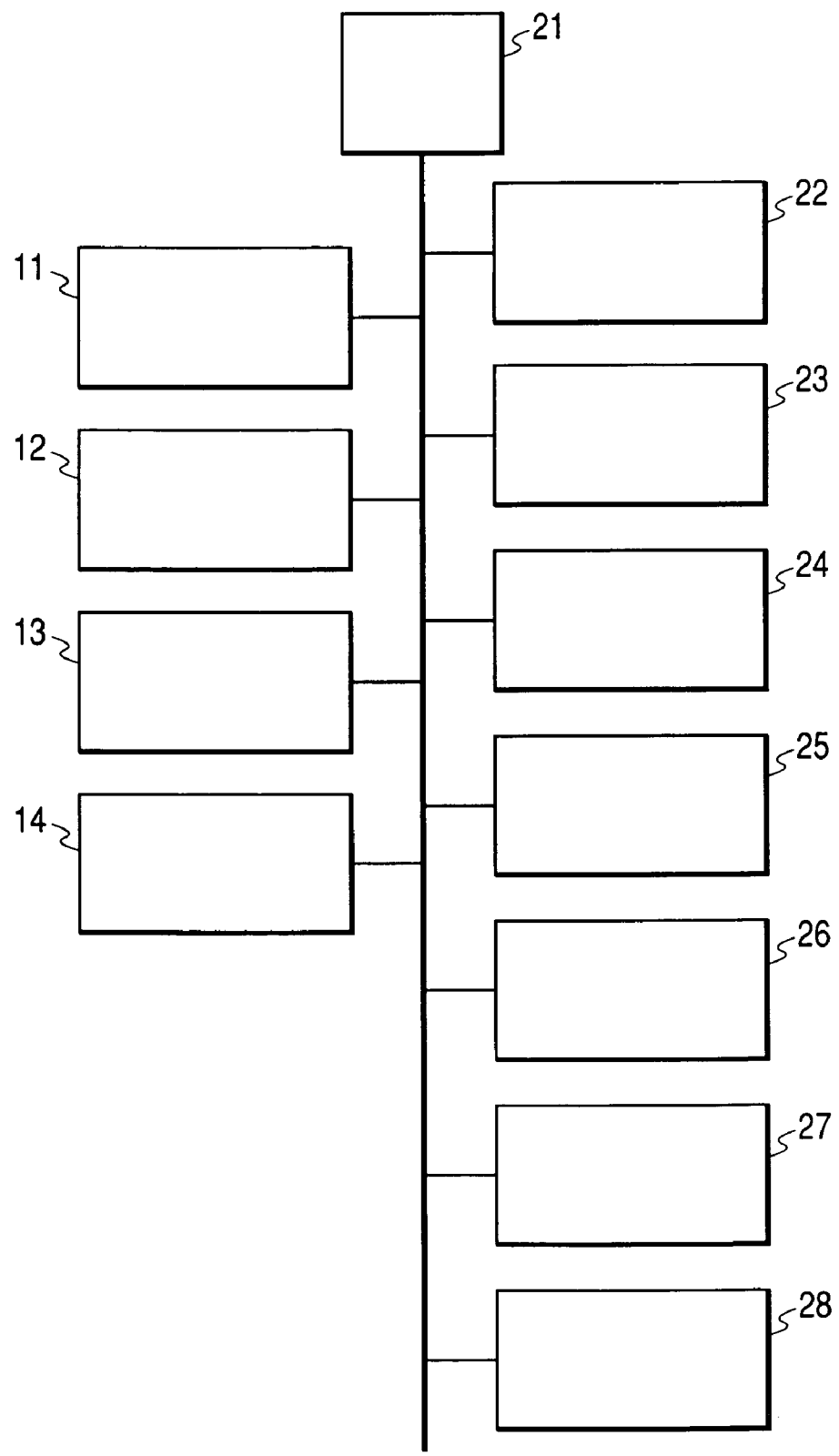
FIG. 3 is a block diagram illustrating the structure of a system.

FIG. 3 is a block diagram showing the structure of a system. The entire system is comprised of a computer system. A BUS 21 is an internal bus in the computer, and connections to the BUS 21 are established from the X-ray generating portion 11, the two-dimensional detector 12, the rotating table 13, the reconstruction portion 15, a pulsation detecting portion 22, a control portion 23 such as a CPU, an image displaying portion 24, a period calculating portion 25, an interface portion 26, a rotation-time calculating portion 27, and a static-ratio determining portion 28, respectively. Thus, transmission and reception of a control signal and data are carried out.

Figure 4:
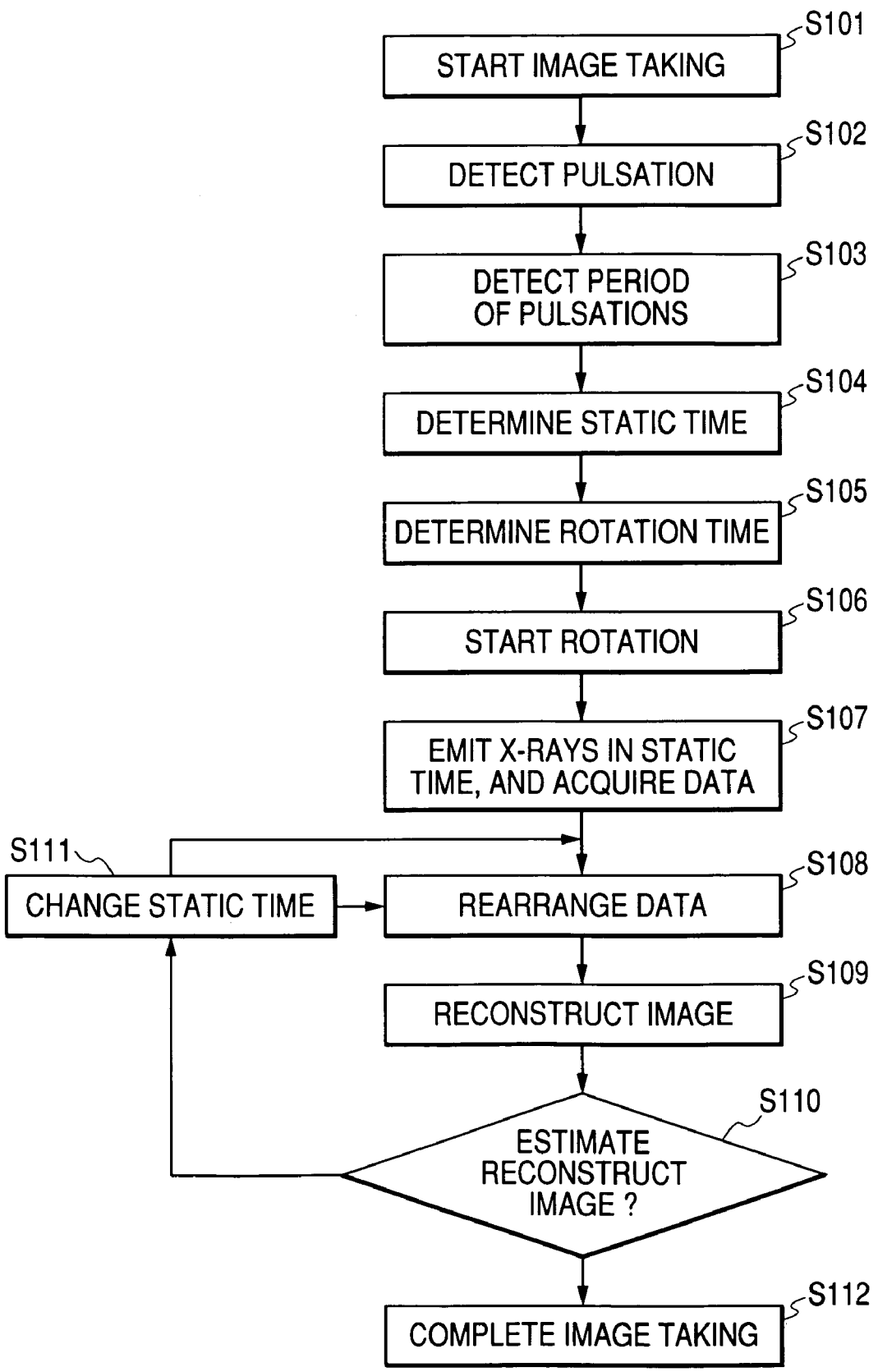
FIG. 4 is a flow chart illustrating a flow of processes.

FIG. 4 is a flow chart showing an image-acquiring procedure. Initially, instructions of start of image-acquiring are supplied through the interface portion 26 (step S101). Upon instruction of the image-acquiring, the pulsation detecting portion 22 detects pulsations of an examined person P (step S102). The pulsation detecting portion can be comprised of an electrocardiograph, a pulse oxymeter for detecting an oxygen forward, or a morphological detecting apparatus in which continuous emission of X-rays is carried out by the X-ray generating portion 11, a distribution of transmitted X-rays is image-acquired by the two-dimensional detector 12, and the size of a heart in the thus-acquired image is detected.

Figure 7:
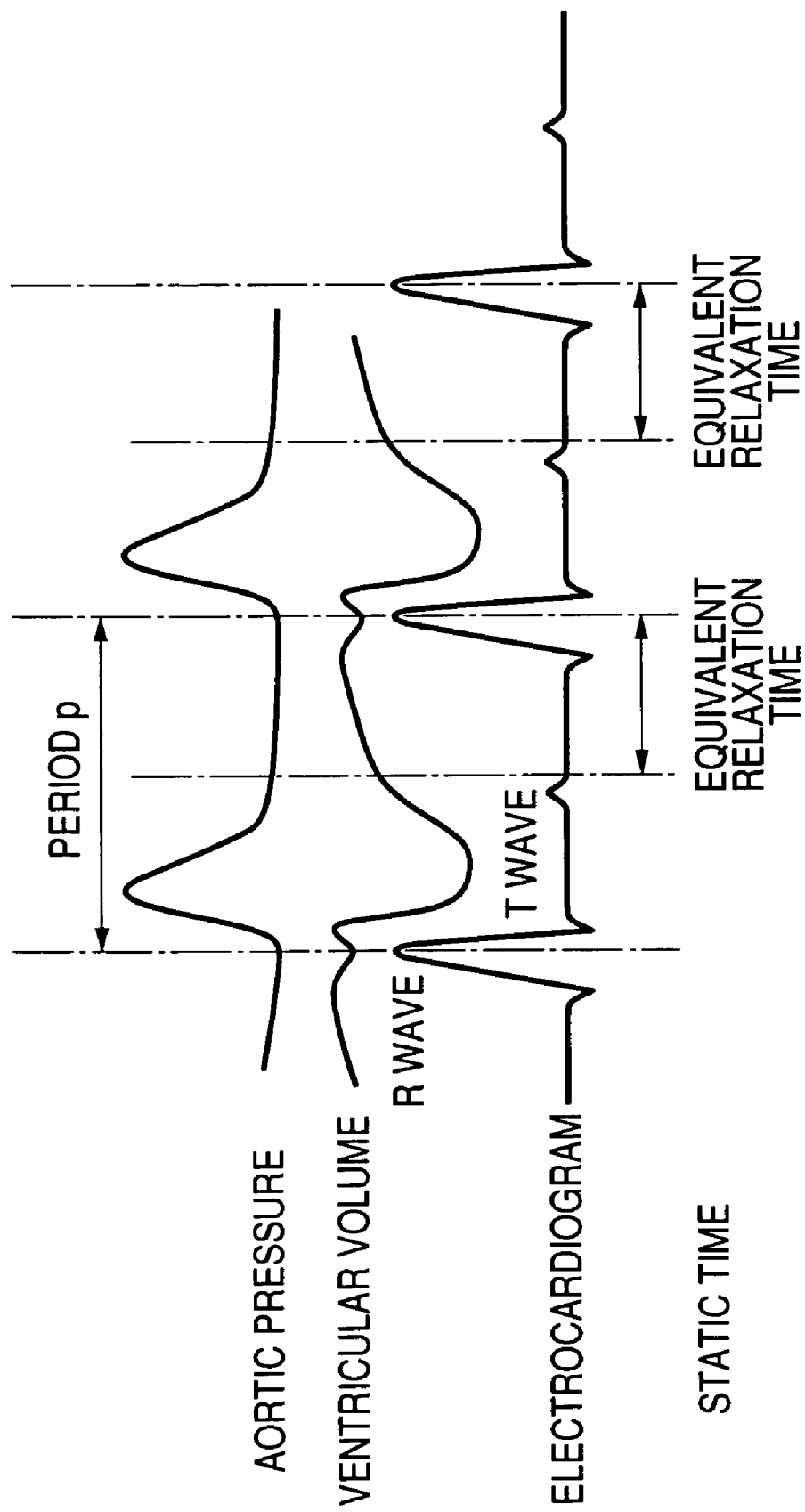
FIG. 7 is a view illustrating a waveform of an electrocardiogram and constriction of a heart.

A periodical signal can be detected by attaching an electrocardiograph or a pulse oxymeter to the examined person P. FIG. 7 discussed above shows a waveform detected by the electrocardiograph. R waves, which are characteristic of a waveform in an electrocardiograph, can be obtained by the period calculating portion 25. A period p of pulsations can be detected by measuring an interval between the R waves (step S103). More specifically, such calculation can be achieved by counting reference pulses appearing between an R wave and an R wave next thereto.

A ratio q of a static time in the pulsation period p is then determined by the static-ratio determining portion 28. The static time is defined by a period in which morphological variations under the influence of pulsations of a heart are small. The morphological change of a heart is classified into a constriction time, a relaxation time and an equivalent relaxation time. The relaxation time is a period in which a volume of a heart is expanded, and the equivalent relaxation time is a period in which the expansion is constricted. The equivalent relaxation time is experimentally determined by reference to the R wave that is characteristic of the static time. As illustrated in FIG. 7, the static time can be determined approximately as a latter half of the pulsation period p that starts from the R wave (step S104).

With respect to the static ratio q (=the equivalent relaxation time) in the pulsation period p determined by the static-ratio determining portion 28, it is restricted as $q \geq 0.5$ in this embodiment. This is because it becomes complicate to take out static data during the scanning operation if q is set less than 0.5. Since the ratio q of the static time is determined in consideration of quality of an image, drastic degradation of a reconstruction image does not necessarily happen when the ratio q is set to be equal to 0.5 (q=0.5), even if an actual ratio q is less than 0.5 or equal to 0.5. To paraphrase it, the limitation of $q \geq 0.5$ does not depart from the purpose of improvement of an image at which the present invention aims at.

Even when a pulse oxymeter is used, it is possible to detect R waves illustrated in FIG. 7. Accordingly, detection of the pulsation period p can be carried out similar to the case of an electrocardiograph. In determining the ratio q of the static time, a delay occurs from a timing of actual pulsations since the pulse oxymeter measures the oxygen forward at a tip of a finger of the examined person. Further, the delay cannot be uniformly determined, since it depends on a body of the examined person and fluidity of blood in blood vessels differs among individuals.

Therefore, in the event that the pulse oxymeter is used, an initial value is given to determine at which phase in the pulsation period p the static time is set. This initial value can be set by determining a highly-frequent value from statistical data base based on information of an examined person P, such as age, height, weight and blood pressure.

A rotation time t for one rotation of the rotating table 13 is then calculated from the pulsation period p and the static ratio q by the rotation-time calculating portion 27, using the following relation.

$t=(n-q)p$ (n is a natural number, and $0.5 \leq q \leq 1.0$)

It is experimentally known that an appropriate rotation time t is 3 (seconds)$\leq t \leq$10 (seconds). If the rotation time t is too short, the examined person P is likely to feel dizzy and move a body, while if the rotation time t is too long, the examined person P becomes impatient and moves a body. Thus, artifact occurs due to the motion of a body. Although there is a case where a plurality of values of n satisfying the relation of 3 (seconds)$\leq(n-q)p \leq$10 (seconds) are present, an appropriate value is selected in accordance with an age of the examined person P (step S105).

Upon determination of the rotation time t, completion of preparation of the image-acquiring is displayed on the interface portion 26. When instructions of start of the image-acquiring are supplied, the rotating table 13 starts to rotate under instructions from the control portion 23 (step S106). The control portion 23 monitors an encoder signal (not shown) generated by the rotating table 13, and confirms if a predetermined uniform speed and a predetermined angle are attained. Upon reaching the predetermined uniform speed and the predetermined angle, a signal is supplied to the X-ray generating portion 11 to start X-ray exposure to the examined person P (step S107). This encoder signal is also used for determination of integral timing of data.

In the event that an encoder capable of generating 25,000 pulses per turn of the rotating table 13 is used, data is acquired from the two-dimensional detector 12 every 25 pulses of the encoder signal when projection data of 1000 views is to be collected during one rotation. The control portion 23 counts those encoder pulses, and generates an integral signal every 25 pulses. The amount of X-rays reaching the two-dimensional detector 12 is thus counted.

Data from the two-dimensional detector 12 is successively transferred to the reconstruction portion 15 through the BUS 21. The transfer of data is continued until the rotating table 13 is rotated by a predetermined rotational angle and a predetermined number of views are collected. Upon rotation of the rotating table 13 by the predetermined rotational angle and acquisition of the predetermined number of views, the control portion 23 instructs the X-ray generating portion 11 to stop the emission of X-rays. After that, the control portion 23 causes the rotating table 13 to reduce the speed, and controls the rotating table 13 until its rotation stops.

Immediately after completion of the emission of X-rays, last projection data is transferred to the reconstruction portion 15. Upon completion of the transfer of projection data, sorting or rearranging processing of data is executed (step S108). Description will be made to the sorting or rearranging processing with reference to FIG. 5. In the relation of $t=(n-q)p$, it is assumed that n=4 and q=0.5. The static time is assumed to be a latter half of the pulsation period p. In a line of the pulsation, a section indicated by E (equivalent relaxation time) is a static time, and this time corresponds to a data area.

When assuming a full scanning in which data is acquired from 360-degree overall directions, it is impossible during the first rotation to use data in areas A0–A1, A2–A3, A4–A5 and A6–A7 since each of these areas is a variation interval. In the second rotation, however, an area A7–A8 corresponds to the area A0–A1 that is the variation interval in the first rotation. In other words, when data in the area A7–A8 is copied for data in the area A0–A1, static-time data in the area A0–A2 is accomplished. Likewise, when data in the areas A9–A11, A11–A12 and A13–A14 are copied for data in the areas A2–A3, A4–A5 and A6–A7, respectively, static-time data for 360 degrees can be acquired.

Figure 5:
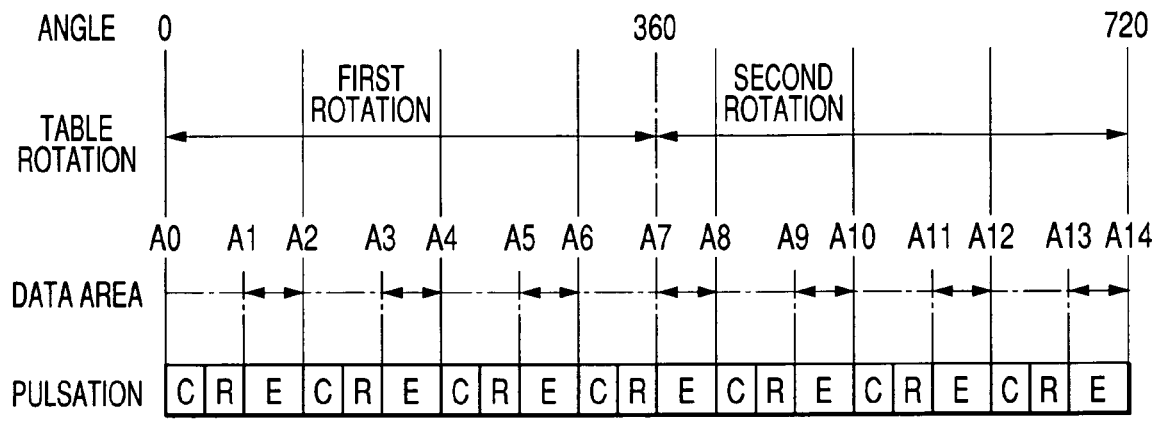
FIG. 5 is a view illustrating a process for acquisition of data, in which a static ratio is determined.
Figure 6:
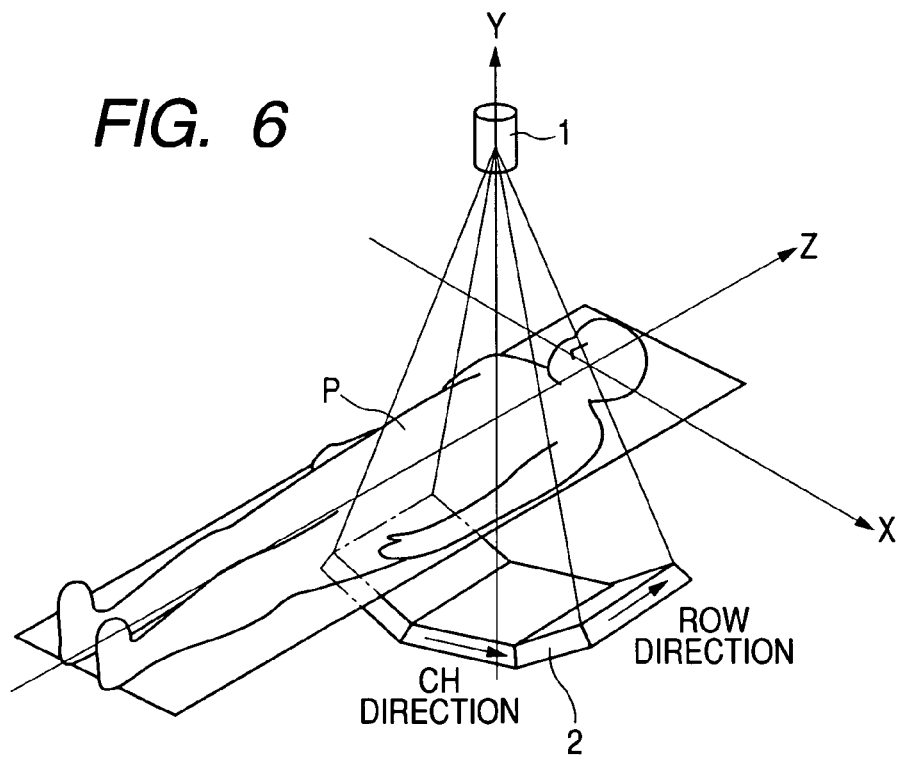
FIG. 6 is a view illustrating a conventional cone-beam CT apparatus.

In the event of a half scanning in which 180 degrees are added to a fan angle, there is no need to completely carry out two rotations. If the fan angle is ten (10) degrees, only acquisition of data over 190 degrees is needed. In the case of FIG. 5, an angle of each area, such as the area A0–A1, is equal to 51 degrees (=360/7 degrees). The reconstruction can be achieved if the static-time data can be collected in the area A0–A4. Accordingly, the scanning operation can be finished at the time when data in the areas A7–A8 and A9–A10 corresponding to the areas A0–A1 and A2–A3 is acquired. Namely, rotation can be finished at the time when acquisition of data is carried out during the rotation from A0 to A10.

In this embodiment, description is made under a condition of q=0.5. In a case of q≧0.5, however, static-time data in the first rotation and the second rotation partly overlap each other. Overlap portions have the same data in principle, and hence either one of them only needs to be used.

In order to reduce the dose of X-ray exposure to the examined person P, the X-ray emission by the X-ray generating portion 11 may be restrictively performed only in the static time. More specifically, the X-ray emission only needs to be carried out in the equivalent relaxation time illustrated in FIG. 5. Further, in the case of q≧0.5, overlap portions of data appear as discussed above, and accordingly there is also no need to carry out the X-ray emission in a time relevant to the overlap portion.

However, limitation of the X-ray emission to the static time only is possible in a case where a phase of the static time in the pulsation period p can be delimited or defined by an electrocardiograph. In a case where the phase of the static time cannot be accurately delimited, such as the case where the pulse oxymeter is used, the X-ray emission cannot be stopped in the static time because there is a need of shifting the static time as discussed above and evaluate a reconstructed image.

The control portion 23 then instructs the reconstruction portion 15 to execute reconstruction based on the rearranged projection data (step S109). The reconstruction is composed of a pre-process, a filter process, and a process of backprojection. The pre-process consists of an offset process, a LOG conversion, a gain correction, and a defect correction. In the filter process, the Ramachandran function or the Schepp-Logan function is generally used, and these are likewise employed in this embodiment. Data subjected to the filter process then undergoes the backprojection.

A Feldkamp algorithm is used as an algorithm from the filter process to the backprojection. Although the Feldkamp algorithm is used as the reconstruction algorithm in this embodiment, the reconstruction algorithm is not limited thereto. There is a reference paper of "Practical Cone-Beam Algorithm", J. Opt. Soc. Am. A1, 612–619, 1984 by Feldkamp, Davis and Kress.

When a CT sectional image is reconstructed after completion of the backprojection, the section is displayed by the image displaying portion 24. As discussed above, an initially-produced reconstruction image undergoes rearrangement based on the initial value of the static time. Therefore, there is a possibility that the reconstruction image contains artifact due to pulsation variations, and the reconstruction image needs to be evaluated (step S110). Although the evaluatation can be carried out by a person, it can also be automatically executed.

In the automatic case, an area near a heart of the examined person is designated, a dispersion of an image in this area is calculated, and this dispersion is compared with a predetermined value. The evaluatation of the image is thus executed. Slicing of an image can be designated by an operator based on the CT image, or can be executed by a process of determining a heart area. In the heart-area determining process, the area can be a predetermined area capable of being predicted from a body shape of the examined person P, or a pattern recognition can be employed. When a person executes it, it is confirmed by the person if artifact appears in a region around the heart area of the reconstruction image.

If the artifact is found, retrial is instructed, and the static time is changed pursuant to the instructions (step S111). The change of the static time is performed by successively shifting the phase of the static time in the pulsation period p. A step width in the shift can be arbitrarily determined, and the width is preferably about a tenth of the pulsation period p, for example.

When a result of the evaluatation does not satisfy a judgment standard, the ratio q of the static time is shifted, and data is rearranged, as discussed above. That loop is repeated until the reconstruction image satisfies the standard relevant to artifact. Finally, the reconstruction image is displayed, and the image-acquiring ends (step S112).

Although it is assumed that X-rays are continuously emitted in this embodiment, a manner of X-ray emission is not limited thereto. It is also possible to generate pulses of X-rays in accordance with integral sections of the two-dimensional detector 12 based on the encoder signal.

According to the present invention, it is possible to reduce artifact due to pulsations of a heart of an examined person and the like, and a system can cope with not only a full scanning operation but a half scanning operation. In the event that a static ratio cannot be delimited or defined, it is possible to improve an image by shifting the static ratio in the data rearrangement operation carried out after completion of the image-acquiring. Further, a rotation time of a table can be preferably determined based on a pulsation period of the examined person.

When the static time in a variation period can be determined prior to the image-acquiring, the radiation dose of X-rays for the examined person can be reduced by executing emission of X-rays only in the static time. Further, even when the ratio q of the static-time relative to the variation period p exceeds 0.5, the radiation dose of x-rays for the examined person can be reduced because overlapping X-ray data can be premeditatedly excluded. Even in a case where a pulse oxymeter or the like is used, it is possible to obtain a reconstruction image without any artifact like a case where an electrocardiograph is used.

As described in the foregoing, according to the present invention, a radiation image-acquiring apparatus or a radiation image-acquiring method capable of removing or reducing influences of variations present in an examined subject can be provided.

The object of the present invention can also be achieved by providing a recording medium (or a storing medium), in which program codes of a software for achieving functions of the above-discussed embodiment is recorded, in a system or an apparatus, and causing a computer (or a CPU, an MPU and the like) in the system or apparatus to read and execute the program codes stored in the recording medium. In this case, program codes themselves read from the recording medium achieve functions of the above-discussed embodiment, and therefore a recording medium recording the program codes is within the scope of the present invention.

Further, there is a case where when program codes read by a computer are executed, functions of the above-discussed embodiment are achieved, and at the same time a portion or all of an actual processing is executed pursuant to instructions of the program codes by an operating system (OS) or the like running on the computer such that functions of the above-discussed embodiment can be achieved by this processing. This case is also within the scope of the present invention.

Furthermore, there is a case where after program codes read from a recording medium are written in a memory provided in an extensions card inserted into a computer, or an extensions unit connected to a computer, a portion or all of an actual processing is executed pursuant to instructions of the program codes by a CPU or the like provided in the extensions card, or the extensions unit such that functions of the above-discussed embodiment can be achieved by this processing. This case is also within the scope of the present invention.

Where the present invention is applied to the above-discussed recording medium, program codes corresponding to the above-discussed flow chart are stored in the recording medium.

As many apparently widely different embodiments of the present invention can be made without departing from the spirit and scope thereof, it is to be understood that the invention is not limited to the specific embodiments thereof except as defined in the claims.

This application claims priority from Japanese Patent Application No. 2003-345209 filed Oct. 3, 2003, which is hereby incorporated by reference herein.

What is claimed is:

1. A radiation image-acquiring apparatus comprising:
X-ray generating means;
two-dimensional detecting means adapted to receive X-rays transmitted through a subject to be examined and converting the X-rays into image data;
rotating means adapted to relatively rotate the subject in an image-acquiring area formed by the X-ray generating means and the two-dimensional detecting means;
variation detecting means adapted to detect a predetermined variation of the subject;
period calculating means adapted to calculate a period p of the variation detected by the variation detecting means; and
static-ratio determining means adapted to determine a ratio q of a static time relative to the period p from the variation detected by the variation detecting means,
wherein rotation-time calculating means calculates a rotation time t for one rotation of the rotating means based on the period p and the ratio q.

2. A radiation image-acquiring apparatus according to claim 1, wherein the ratio q of the static time relative to the period p is set so as to satisfy a relation of $0.5 \leqq q \leqq 1.0$.

3. A radiation image-acquiring apparatus according to claim 2, wherein the rotation time t is set so as to satisfy a relation of $t=(n-q)p$ (n is a natural number).

4. A radiation image-acquiring apparatus according to claim 3, wherein the rotation time t is set so as to satisfy a relation of $3(\text{seconds}) \leqq t \leqq 10(\text{seconds})$.

5. A radiation image-acquiring apparatus according to claim 1, wherein the variation detecting means detects the variation by an electrocardiograph or a pulse oxymeter, or based on a transmission image obtained by the two-dimensional detecting means.

6. A radiation image-acquiring apparatus according to claim 1, wherein the X-ray generating means emits X-rays toward the subject only in the static time.

7. A radiation image-acquiring apparatus according to claim 1, wherein a phase of the static time in the period p is changed based on a reconstruction image.

8. A radiation image-acquiring method performed in a radiation image-acquiring apparatus including X-ray generating means, two-dimensional detecting means adapted to receive X-rays transmitted through a subject to be examined and converting the X-rays into image data, and rotating means adapted to relatively rotate the subject in an image-acquiring area formed by the X-ray generating means and the two-dimensional detecting means, said method comprising:
a variation detecting step of detecting a predetermined variation of the subject;
a period calculating step of calculating a period p of the variation detected in the variation detecting step; and
a static-ratio determining step of determining a ratio q of a static time relative to the period p from the variation detected in the variation detecting step,
wherein a rotation time t for one rotation of the rotating means is calculated based on the period p and the ratio q in a rotation-time calculating step.

* * * * *